(12) United States Patent
Magner et al.

(10) Patent No.: US 7,833,414 B2
(45) Date of Patent: Nov. 16, 2010

(54) POLAR FOG WASTE TREATMENT

(76) Inventors: Joseph Magner, 621 Mayfair Ave., South San Francisco, CA (US) 94080; Richard V. York, 405 Paine Rd., Castle Rock, WA (US) 98611

( * ) Notice: Subject to any disclaimer, the term of this patent is extended or adjusted under 35 U.S.C. 154(b) by 0 days.

(21) Appl. No.: 12/550,169

(22) Filed: Aug. 28, 2009

(65) Prior Publication Data
US 2009/0314709 A1 Dec. 24, 2009

Related U.S. Application Data

(63) Continuation of application No. PCT/US2008/054698, filed on Feb. 22, 2008.

(60) Provisional application No. 60/892,068, filed on Feb. 28, 2007.

(51) Int. Cl.
*C02F 3/28* (2006.01)
*C02F 11/04* (2006.01)

(52) U.S. Cl. ...................... 210/603; 210/613

(58) Field of Classification Search ............... 210/603, 210/612, 613
See application file for complete search history.

(56) References Cited

U.S. PATENT DOCUMENTS

| | | | | |
|---|---|---|---|---|
| 3,617,538 | A | * 11/1971 | Bogert | ............ 210/612 |
| 4,372,856 | A | 2/1983 | Morrison | |
| 4,559,142 | A | 12/1985 | Morper | |
| 4,721,569 | A | 1/1988 | Northrop | |
| 4,784,770 | A | * 11/1988 | Nagao | ............ 210/603 |
| 4,871,283 | A | 10/1989 | Wright | |
| 5,290,450 | A | * 3/1994 | Kobayashi | ............ 210/603 |
| 6,224,646 | B1 | 5/2001 | Arato et al. | |
| 6,464,875 | B1 | 10/2002 | Woodruff | |

(Continued)

FOREIGN PATENT DOCUMENTS

| | | |
|---|---|---|
| JP | 2002-153897 | 5/2003 |
| WO | WO 89/00548 | * 1/1989 |

OTHER PUBLICATIONS

PCT/US2008/54698—PCT International Search Report, mailed Jul. 30, 2008.

(Continued)

*Primary Examiner*—Fred Prince
(74) *Attorney, Agent, or Firm*—Reed Smith LLP; Craig P. Opperman

(57) ABSTRACT

A FOG waste treatment facility includes a slipstream loop incorporating circulation pumps, heat exchangers and anaerobic digesters for continuously circulating actively digesting sludge at a rate to preclude solid settlement accumulation warmed actively digesting sludge is pumped from the slipstream loop through a rock trap into a delivery/input loop both for aiding delivery of FOG waste to, and for partially filing, a receiving/conditioning holding tank. The actively digesting sludge softens and liquefies the FOG wastes offloaded into the holding tank for further treatment at a desired treatment temperature range. The contents of the receiving/conditioning holding tank are continuously mixed by a bottom-top recirculation chopper pump to pre-treat the FOG wastes, and decreasing solids particle size. The produced, flowable feedstock slurry can then be injected back into the actively digesting sludge slipstream loop at a controlled rate. The resultant mixture then is introduced into the input of waste treatment systems having anaerobic digesters for digestion of solids.

57 Claims, 2 Drawing Sheets

U.S. PATENT DOCUMENTS

| | | |
|---|---|---|
| 6,692,642 B2 | 2/2004 | Josse |
| 6,838,000 B2 | 4/2005 | Braun |
| 6,893,556 B2 | 5/2005 | Yaegashi et al. |
| 2003/0094002 A1 | 5/2003 | Hibino et al. |
| 2003/0155295 A1* | 8/2003 | Le .................... 210/603 |
| 2005/0056588 A1 | 3/2005 | Petering |
| 2006/0004237 A1 | 1/2006 | Appel et al. |
| 2006/0096163 A1 | 5/2006 | Dickinson et al. |
| 2006/0175252 A1 | 8/2006 | Upendrakumar et al. |
| 2006/0289356 A1 | 12/2006 | Burnett et al. |
| 2007/0095734 A1 | 5/2007 | Lee |
| 2007/0098625 A1 | 5/2007 | Adams et al. |

OTHER PUBLICATIONS

Chevron Energy Solutions Company, a Division of Chevron U.S.A. Inc.; "Cogeneration & Grease Receiving Station Project—Report and Proposal"; Dated Feb. 3, 2005; pp. 17-20, and Attachment 1 pp. 2-5 of Detailed Scope of Work.

Chevron Energy Solutions Company, a Division of Chevron U.S.A. Inc. and the City of Millbrae, CA; "Energy Services Contract"; Dated Apr. 27, 2005, Attachment D—Scope of Work pp. 2-5.

* cited by examiner

POLAR FOG WASTE TREATMENT

RELATED APPLICATIONS

This application is a continuation of PCT Application No. PCT/US2008/054698 filed Feb. 22, 2008, which is related to and claims priority from U.S. patent application Ser. No. 11/683,877, (now U.S. Pat. No. 7,485,230) filed on Mar. 8, 2007, and which is incorporated herein by reference in its entirety, and claims priority under 35 U.S.C. §119(e) from U.S. Provisional Patent Application No. 60/892,068 filed on Feb. 28, 2007, and which is also incorporated herein by reference in its entirety.

BACKGROUND

1. Field of the Invention

The invention relates to integrated digestible wastes (sewage and otherwise) and waste polar fats/oils/greases/waxes (FOG) treatment methods, systems and facilities including anaerobic digesters and steady-state generation of methane.

2. Description of the Prior Art

Excessive concentrations of FOG (fats, oils, waxes and greases) are a major problem in wastewater/sewage collection and treatment systems. There are two types of FOG. The first type, polar FOG originates from animals or vegetable (foods). Because of the prevalence of food service and processing enterprises in populated environs, polar FOG is responsible for a large percentage of sewer system failures and overflows. In particular, polar FOG, if not intercepted congeals on and sticks to piping and fixtures in wastewater systems, and, as well, to other debris flowing in the waste stream creating plugs and causing functional failures of the sewer system components.

The second type, non-polar FOG, is from petroleum or mineral origins, i.e., is petroleum-based oils, waxes, and greases. This type of FOG is typically detrimental to wastewater treatment systems/processes and, in particular, to the biologic phase of waste treatment process inhibiting (poisoning) microorganisms that breakdown or digest the wastes. Introduction of non-polar FOG into a sewage treatment system is generally prohibited by law and penalized when possible.

Publicly owned sewage treatment systems typically, by statutes, ordinances, and/or regulations, require food service and processing enterprises discharging waste in to public systems to have, and regularly maintain grease traps and interceptors to prevent introduction of generated polar FOG into treatment systems. Grease traps and interceptors are baffled tanks or basins that functionally rely on the immiscibility and the different densities of wastewater and FOG. Wastewater with FOG and other materials are input near the tank top and pools on one side of the baffle(s). The wastewater flows the beneath the baffles trapping less dense FOG floating, cooling and congealing on the water surface behind the baffle. The more dense and FOG'ed (coated) solid materials input with the wastewater settle to the tank bottom. Wastewater exits the tank near the top on the opposite side of the baffle(s) for the most part, sans low density FOG and other high-density materials. However, grease traps and interceptors have limited capacities. The accumulated, floating and congealed FOG and heavier coated materials settled on the tank bottom must be regularly removed, otherwise the trap/interceptors can plug up. Or more seriously, as the traps/interceptors approach capacity, input wastewater tends to entrain both FOG and other materials as it streams through the FOG/solids filled trap/interceptor tank inducing failures downstream in the sewer system.

Best management practices taught by publicly owned wastewater treatment operations mandate regular clean outs of both grease traps and interceptors preferably by professional FOG haulers and recyclers licensed for handling and properly disposing of 'BROWN' FOG, i.e., polar FOG contaminated with raw sewage and solids that typically collect in grease traps and interceptors. The simplest and probably most economical mode of cleaning out grease traps and interceptors is to isolate the trap/interceptor in the plumbing system, and then to pump or 'vacuum' the entire contents of the trap or interceptor tank/basin into a truck or trailer tank. Caked grease/fat is then steam or pressure-cleaned from the interior tank/basin walls with the wash accumulate being vacuumed into the truck or trailer tank. The so tanked 'BROWN' FOG evacuate from grease traps/interceptors is an unholy, difficult to handle, smelly, watery, sticky mess.

Properly disposing of such tanked 'BROWN' FOG evacuate is a problem precisely because it is contaminated, contains rocks, glass, tableware, both broken and not, bones and other items people thoughtlessly, or purposely toss/flush down drains at public and commercial establishments. Historically, such 'BROWN' FOG evacuate has been deemed 'toxic' and is required to be disposed of in landfills appropriately isolated from aquifers and surface drainages. Existing appropriate disposal sites are filling up, and new sites are difficult to find, and once found, economically expensive to establish and maintain. Finally, after a landfill site reaches capacity, its possible uses are limited far into the foreseeable future.

It is well recognized in wastewater management fields that 'BROWN' FOG also comprises a source of feedstock suitable for digestion, with the benefits of biogas production including methane for electrical power generation and heating. For example, the South Bayside System Authority (SBSA) located in Redwood City, Calif. has been accepting 'BROWN' FOG evacuate from 13 or so permitted haulers since the early 1990's at rates of 1500 to 3000 gallons per day, that after removal of indigestible solids (rocks, glass & tableware) produce approximately 20 cubic feet of digester gas (60% methane) per gallon of greases when introduced into a single mesophilic anaerobic digester. Problems experienced at the SB SA facility primarily relate to handling of the 'BROWN' FOG evacuate, and to spiking of biogas production with each cleaned 'BROWN' FOG evacuate loaded into the digester. The Wastewater Division of the City of Oxnard, Calif. (OWD) actually provides a municipal grease trap/interceptor cleanout service with personnel and vacuum trucks for local food servicing and processing enterprises. The collected 'BROWN' FOG evacuate is input via grease feed and horizontal chopper pumps to one of three 110 foot anaerobic digesters where mixing is enhanced using gas draft tubes. Again, the problems experienced at the OWD treatment plant, akin to those at SBSA, relate to material handling (clogs) and spiking biogas production when the 'BROWN' FOG evacuate is offloaded to the digester.

SUMMARY OF THE INVENTION

An invented integrated cogeneration digestible wastes, and polar fats/oils/greases/waxes (FOG) waste treatment method, system and facility is described that includes a warmed sludge, slipstream loop incorporating circulation pumps, a hot water heat exchanger and a conventional anaerobic digester system continuously circulating actively digesting sludge from the bottom or base of the digester system, and then back to the top or head end of the digester system at a rate for precluding solid settlement accumulation as a warm flowable slurry source. The actively digesting sludge is warmed by the heat exchanger at least to a temperature sufficient to soften and/or liquefy polar FOG. The warmed, actively digesting sludge is pumped from the slipstream loop through a rock trap and a delivery/input line (i) for aiding transport of delivered 'BROWN' and/or 'YELLOW' FOG wastes offloaded via a rock trap from a tank hauler via a hose connected to the rock trap and the input line, and (ii) for partially filling a closed, vented, receiving/conditioning holding tank with offloaded FOG and actively digesting sludge. The offloaded FOG waste and the actively digesting sludge in the closed, vented, receiving/conditioning holding tank, are continuously mixed by a bottom-top, recirculation, chopper pump to pre-treat the FOG wastes, liquefying, hydrolyzing and decreasing solids particle size to allow acidogens in the sludge to pre-digest such wastes producing volatile fatty acids, some biogas and a highly bioreactive, flowable, feedstock slurry. The highly bioreactive, flowable, feedstock slurry is then injected back into the warmed sludge slipstream loop at a controlled (metered) rate, whereupon the mixture is introduced, together with raw sewage or other digestible wastes, into the top or head end of an anaerobic digester system for solids digestion and steady-state methane production.

Advantages of the integrated system relate to (i) a positive net energy gain from increased steady-state methane production suited for electricity generation using micro-turbines, or for combustion as a thermal energy source and/or for storage, and to (iii) significantly reduced solids volume output of both the treated sewage/digestible wastes and FOG wastes.

Novel aspects of the invented integrated system relate to the pre-treatment circulation of 'BROWN' and 'YELLOW' FOG waste and the actively digesting sludge in the storage/reaction holding tank for partial digestion of the FOG, generating volatile fatty acids that suppress expression of sludge methane producing methagens in the reaction/holding tank while simultaneously converting the sticky, gooey FOG and digesting sludge into a miscible, highly bioreactive, flowable, feedstock slurry ideally suited for driving anaerobic digestion of raw sewage and other digestible wastes.

Other novel aspects of the invented integrated generation system relate to the maintenance of ratios of the offloaded FOG waste volume to actively digesting sludge input into the receiving/conditioning holding tank.

An important feature of the invented integrated cogeneration system is that the actively digesting sludge is input into the delivery input line immediately upstream from a rock trap sieving offloading tanked 'BROWN' FOG accumulate just before and just after the FOG waste is offloaded from a tank truck. This process assures the delivery/input line is always warm and pre-coated with actively digesting sludge before the sticky FOG is offloaded, and is subsequently scoured by the actively digesting sludge after the sticky FOG is offloaded removing any adhering greases/oils/fats/waxes and particulate in the line thereby essentially eliminating possibilities of a clog-up during subsequent offloads.

Still other novel aspects of the invented integrated cogeneration system relate to automating offloading processes, automating filling, circulation, and metering flowable the miscible, highly bioreactive, feedstock slurry from the receiving/conditioning holding tank, and automating temperature maintenance processes within the actively digesting sludge slipstream loop.

Still other aspects of the invented integrated cogeneration system affords servo control for optimizing both digestion processes in the digesters and steady-state methane production for electrical power generation inherent in the capacity to meter introduction of a highly bioreactive, flowable feedstock slurry from the reaction/holding tank into the continuously circulating warm, actively digesting sludge slipstream loop for introduction with sewage and/or other digestible wastes into anaerobic digester systems.

It also should be appreciated that while the invented integrated cogeneration system is presented in context of anaerobic primary and secondary digesters, an AGMM system, the invented processes and systems are equally applicable to any sewage treatment systems having an anaerobic digester in schemes that include aerobic and other types of digesters, e.g. AGTM and AGMT systems.

DETAILED DESCRIPTION OF EXISTING AND PREFERRED EMBODIMENTS

Figure 1:
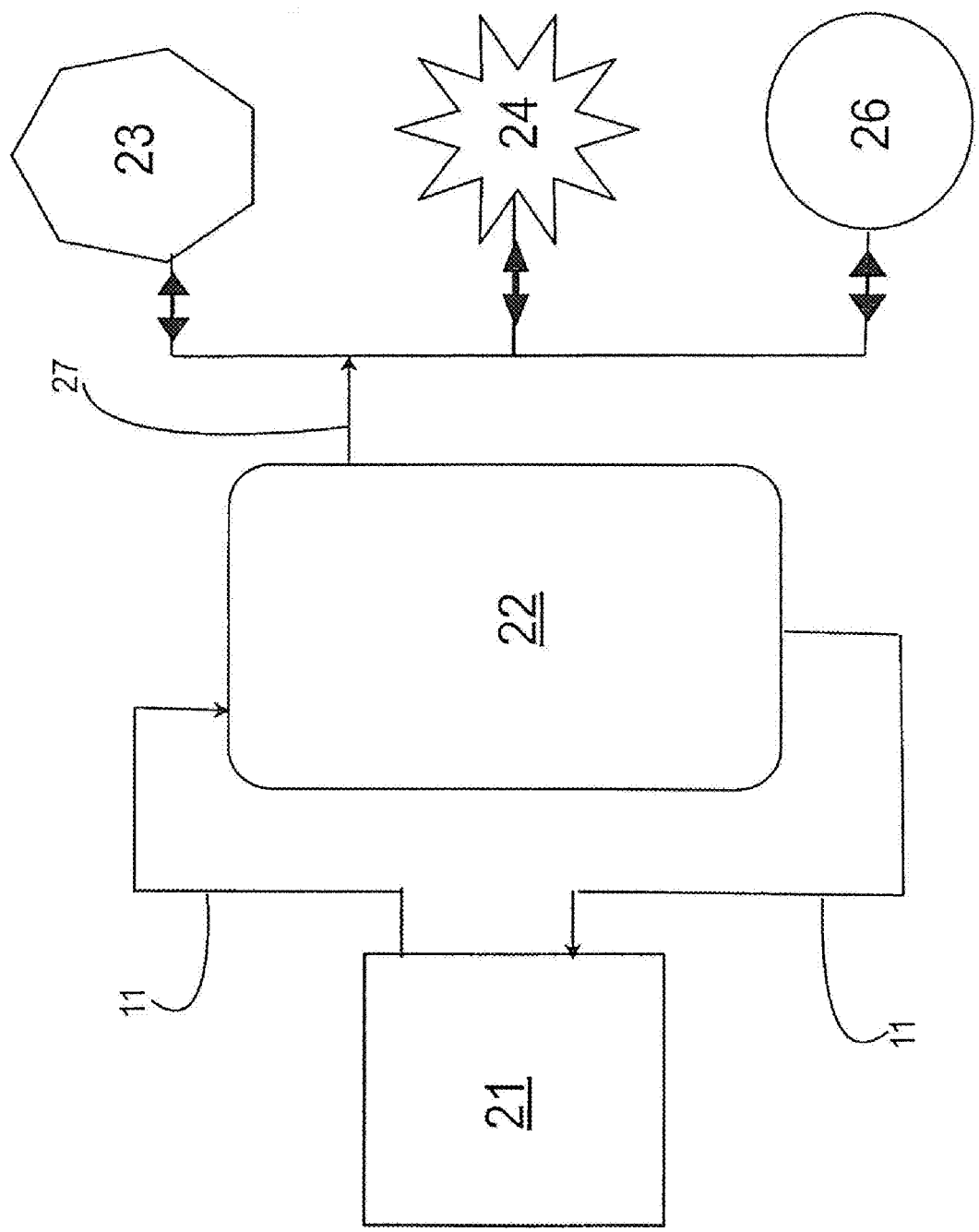
FIG. 1 is a block diagram showing the FOG receiving/pre-treatment station, the digestible wastes processing system, and output utilization of produced methane.

Looking at FIG. 1 the invented integrated cogeneration system for treating raw sewage, and polar fats/oils/greases/waxes (FOG) wastes includes a FOG receiving and pre-treatment station 21 receiving actively digesting sludge circulating in a slipstream loop 11 from the base or bottom of a digestible wastes treatment facility 22, and outputting a highly bioreactive, flowable, feedstock slurry mixed with actively digesting sludge circulating in the slipstream loop 11 to the top or head/input end of the wastes treatment facility 22. Produced methane gas is either used to generated electrical power 23, combusted to produce thermal energy 24, or stored 26 for future use.

The wastes treatment facility 22 is located in Millbrae, Calif. and is an Acid/Gas Mesophilic acid phase—Mesophilic gas phase (AGMM) system where a primary anaerobic digester receives raw sewage, and pours over to a secondary anaerobic digester. The overall objective of the integration was to increase steady-state methane production 27 at the facility at no cost to rate payers for purpose of driving a micro-turbine electrical power generator 23 for increased electrical power generation at the facility, and to reduce solids volumes from the digesters, while providing a fee generating service capable of receiving and processing so called 'BROWN' FOG evacuate from grease traps/inceptors tanked on tucks and/or trailers by licensed FOG haulers servicing food service and processing enterprises in the San Francisco Bay region and surrounding areas.

In January, 2007 construction of the Millbrae facility was essentially completed, and shakedown operations and processes testing and experimentation with constructed system began. Those operations, tests and experimentations are ongoing during preparation of this application. The purpose of the shakedown operations, and testing and experimentation is to determine optimal operating conditions for the unique parameters at the Millbrae facility. In particular, every sewage treatment facility has its unique populations of digesting flora that depend on system operating parameters and the diverse nutrients, chemistries, temperatures, and other biological factors in the incoming wastewater and waste streams being treated.

Figure 2:
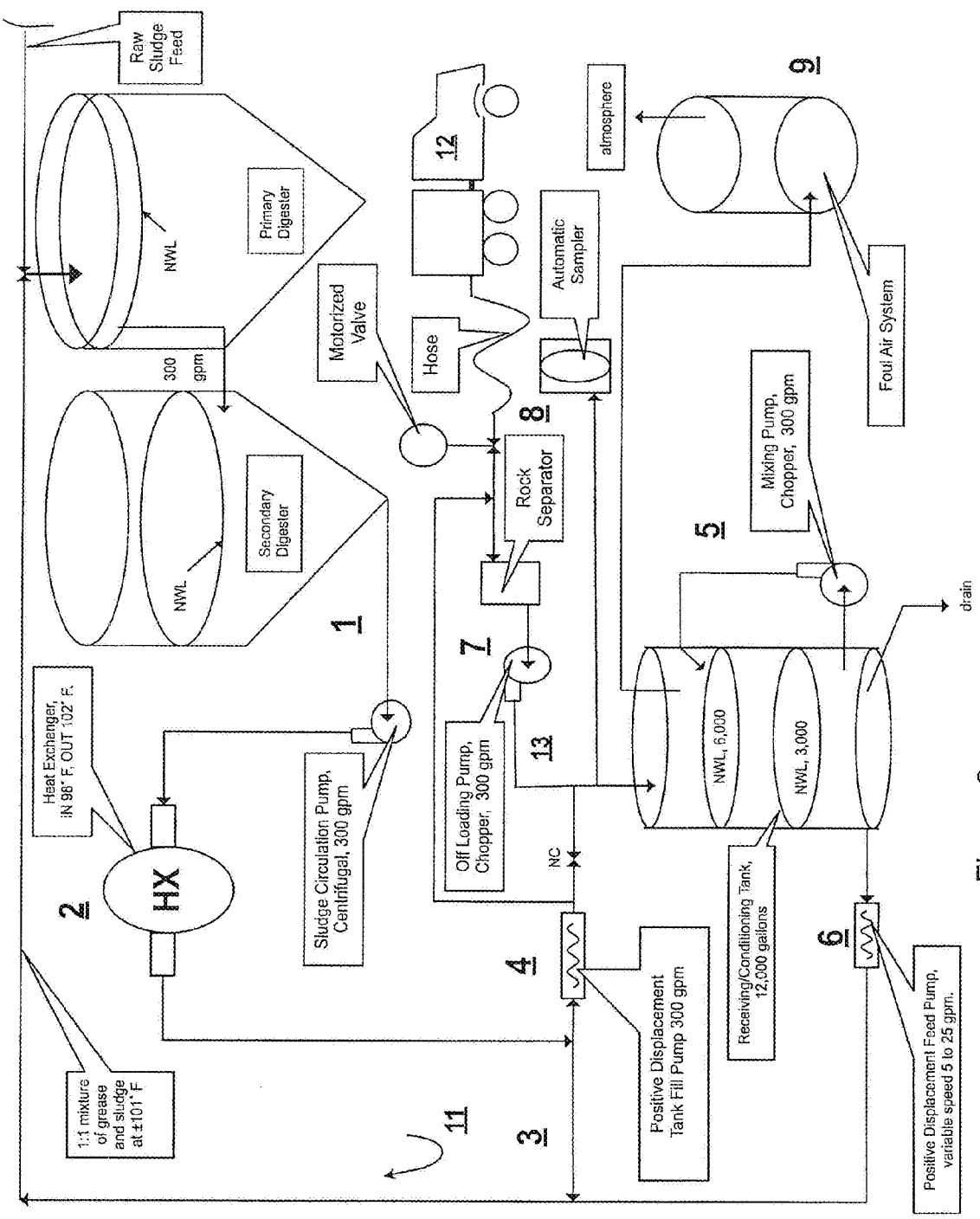
FIG. 2 presents a labeled diagram of the invented integrated cogeneration system for treating raw sewage, and polar fats/oils/greases/waxes (FOG) wastes designed by, and constructed under the direction the Applicants at the Water Pollution Control Plant for the City of Millbrae, Calif. located at the 400 East Millbrae Avenue at the east end of the on-ramp to Interstate 101.

The applicants contend that their invented process and systems for receiving, processing and introducing 'BROWN' FOG evacuate from grease traps/inceptors or even collected 'YELLOW' FOG, i.e. polar fats/oils/greases/waxes not contaminated with raw sewage, for cogeneration of methane and associated electricity can be integrated into any wastewater treatment facility having an anaerobic digester in its treatment scheme including but not necessarily limited to Acid/Gas Thermophilic acid phase—Mesophilic gas phase (AGTM) systems; and Acid/Gas Mesophilic acid phase—Thermophilic gas phase (AGMT) systems As indicated in greater detail in the labeled flow diagram of FIG. 2, the constructed system includes a warmed sludge slipstream loop indicated by the arrow 11 that flows from the bottom or base of a secondary anaerobic digester, includes a 300 gpm sludge circulation pump 1, a hot water heat exchanger 2, and that then returns back 3 to the top or head of a primary digester. As indicated, actively digesting sludge is withdrawn from the base of the secondary digester is warmed to temperatures of up to 104° F. (40° C.) and is circulated in the loop at rates up to 300 gpm. A positive displacement pump 4 also having a capacity of up to 300 gpm, on demand, pumps the warmed, actively digesting sludge from the slipstream loop through a rock separator 8, an offloading chopper pump (with a similar pumping capacity of up to 300 gpm) through a delivery/input piping 13 to a closed, vented, receiving/conditioning holding tank 5. A bottom-top recirculation chopper pump circulates from bottom-to-top, contents pumped into the receiving/conditioning holding tank 5 for pre-treating and conditioning the FOG wastes, liquefying, hydrolyzing and decreasing solids particle size and inducing the acidogens in the sludge to pre-digest such wastes to produce volatile fatty acids, some biogas and a miscible, highly bioreactive, flowable FOG/sludge feedstock slurry. Biogas produced in the receiving/conditioning holding tank 5 is vented from the holding tank and is scrubbed 9 to remove possible offending odorants and thereafter preferably burned for producing energy.

A second positive displacement pump 6 injects the bioreactive, miscible, FOG/sludge, flowable feedstock slurry pumped from near the base of the holding tank back into the warmed sludge slipstream loop 11 at a meterable rate from 1 gpm up to 25 gpm, whereupon it circulates in the slipstream piping mixing with the actively digesting sludge and then is introduced with the sludge along with raw wastewater sewage and/or other digestible wastes into the head or input end of anaerobic digesters for reducing solids output and greatly increasing steady-state methane production from the digesters.

The volume ratio of warmed, circulating actively digesting sludge to the volume of the flowable and miscible FOG/sludge feedstock slurry injected from the holding tank 5 back into the slipstream loop should be maintained such that the acidogens and volatile acids in the slurry are buffered minimizing inhibition of the methagens carried by the circulating, actively digesting sludge in the slipstream loop.

In more detail as indicated in FIG. 1, polar FOG wastes, 'BROWN' and/or 'YELLOW', are pumped from a tank hauler 12 operated by a licensed commercial hauler, via a hose connecting to a rock trap 8 by an offloading pump 7 into the receiving/conditioning holding tank 5. In particular, the hauler pulls onto an offloading drain basin bib. A motion sensor will activate a camera for documenting the offloading event, and, if dark, turn on lights to illuminate the area. The commercial hauler starts the process by swiping an authorizing and identifying magnetic ID card for capturing an account number, driver name, truck serial number, before allowing access to a hose box, and then initiates recording of receipt manifests for evidencing delivery/receipt of the load.

When continuity is sensed between the hose connection and tanker truck (via a ground clamp), a traffic gate is lowered to remind the hauler that the tanker is connected to hose and to open a manual block valve. Once the manual block valve is opened, the offloading sequence is enabled.

In particular, the first positive displacement tank fill pump 4 will initially discharge a sufficient quantity of the warmed, actively digesting sludge into the rock separator 8 to warm and coat the rock separator 8, the offloading chopper pump 7 and the input line piping 13 to the closed, vented, receiving/conditioning holding tank 5. However, the FOG receiving system is pre-programmed such that the positive displacement tank fill pump 4 automatically maintains a minimum volume ($V_1$) in the holding tank, i.e. at a level in the holding tank 5 higher than the second positive displacement metering pump 6 outlet. Once temperature in the input line 13 is achieved, a motorized block valve opens and the chopper pump activates to offload the FOG from the tank hauler 12. The FOG evacuate is periodically sampled by an automatic sampler as it is offloaded.

To preclude any possibility of back filling the tank hauler 12 with liquids circulating in the system facilities, an interlock on the motorized valves shuts off the sludge circulation pump 1, both positive displacement pumps 4 & 6 and the bottom-top recirculation chopper pump 5 recirculating and mixing the contents in the holding tank 5. The tank truck hauler 12 initiates a wash cycle to assure a complete offloading of the FOG using a pressure steam or hot water wash system (not shown) either associated with the tank hauler 12 or made available at the drain basin bib. In the event of a spill, piping (not shown) connects the offloading pump 7 for pumping spilled FOG wastes and associated liquids from the drain basin bib.

A sensor in the holding tank 5 senses a starting level in the tank upon initiation of the offloading by the chopper pump 7, and an ending level upon completion of the offload, i.e., when the tank level ceases to rise over an appropriate time interval. A delivered volume ($V_H$) is then calculated and printed on the manifest delivery receipt for the hauler and recorded in separate manifest received record maintained by the treatment facility. The motorized offloading block valve then begins to close and interlocks shuts down the offloading chopper pump 7. Once the motorized block valve is fully closed, the sludge circulation pump 1, the positive displacement pumps 4 & 6, and the bottom-top recirculation chopper pump all resume pumping. The positive displacement pumps 4 immediately starts pumping warmed, actively digesting sludge from the slipstream loop into the receiving/conditioning tank for flushing and scouring the rock trap and offloading input piping 13 and then adds a specific volume ($V_2$) of the warmed, actively digesting sludge to the holding tank 5 to establish a specified sludge to offloaded FOG volume ratio.

To explain, there will be an existing volume of the already fully, or not so fully conditioned flowable, bioreactive FOG feedstock slurry, or just actively digesting sludge in the holding tank 5 at a particular (lower) temperature than that of the warmed actively digesting sludge circulating in the slipstream loop. The offloaded raw FOG further cools the holding tank contents, While the acidogens are quite hardy and resilient to temperature swing, there are optimum conditions that relate to temperature, mixing achieved by the bottom-top recirculation mixing chopper pump, the acidogens in the newly input actively digesting sludge and the nature of the FOG offloaded. The Applicants suggest volume ratios of the flowable miscible, bioreactive FOG/feedstock slurry with actively digesting sludge already in the holding tank ($V_1$): the FOG volume ($V_H$) offloaded into the holding tank: the subsequent volume ($V_2$) of warmed, actively digesting sludge thereafter added to the holding tank be set at 1:1:1 as a starting point for testing and experimentation to determine optimum conditions for pre-treating/conditioning the FOG and actively digesting sludge in the holding tank. The objective of the testing and experimentation is to create a highly bioreactive, flowable, feedstock slurry in the holding tank that is optimized for continuous anaerobic digestion together with raw treatable/digestible wastes, including but not limited to sewage, in the waste processing/treatment systems of the particular facility for reducing solids output and increasing steady-state methane production.

Periodically, warmed, actively digesting sludge from the slipstream loop should be pumped into, almost filling the holding tank 5 and circulated by the bottom/top mixing pump in the tank 5 for a set time-period to scour and flush the holding tank. Sewage system operators should also appreciate that maintaining a set minimum volume ($V_1$) or level of liquid in holding tank in the manner described, automatically fluctuates the volume of introduced actively digesting sludge in the tank over time. That is, when the holding tank level drops to a predetermined low level, the tank fill pump 4 comes on to fill the holding tank to the predetermined minimum volume ($V_1$). In this way, the meterable feed pump 6 injecting the holding tank contents back into the circulating slipstream loop can be run continually, and the FOG receiving station system components may be flushed clean by introduced actively digesting sludge between offloads of FOG delivered by tank haulers to the system.

The advantages of the invented integrated system of a FOG receiving and pre-treatment station with a two-phase mesophilic acid phase and mesophilic gas phase wastewater treatment facility is that it is a simple system to operate and maintain manually, and is easily amenable to automation and automatic operation using programmable logic controllers (PLC).

Skilled sewage system operators should also appreciate that the receiving/conditioning holding tank essentially comprises an acid phase digester ideally suited for digesting 'BROWN' and 'YELLOW' polar FOG wastes using actively digesting sludge for creating a highly bioreactive, flowable, feedstock slurry that can be stored, further concentrated, and even tanked and transported to other locations as fuel for other anaerobic waste digestion systems, driving digestion of wastes other than sewage, to reduce the output volume of digested solids and increase steady-state methane production (energy generation) by such systems. In fact, initial measurements of stored, fully conditioned, highly bioreactive, flowable, feedstock slurry taken from the receiving/conditioning holding tank at the Water Pollution Control Plant in Millbrae, Calif. indicate that the stored bioreactive feedstock slurry does not produce or outgas any gases, in particular methane, meaning that all methagens in the actively digesting sludge mixed and conditioned with the FOG in the holding tank were eradicated by the low pH fatty acids produced by acidogens in the sludge in an acid phase digestion of the FOG wastes occurring in the holding tank.

The invented system also avoids problems of emulsified grease at the input or head end of the waste digestion cycles in a treatment plants. In particular, FOG from grease traps and interceptors transported in tank haulers from collection points to the treatment plants will always have a component of emulsified FOG in the accompanying wastewater due to the nature of washing and cleaning procedures of grease traps/interceptors by the waste haulers and the sloshing and vibration experienced during tank transport. Precluding emulsified grease from entering wastewater plant treatment processes is a highly recommended, promoted and regulated best management practice for sewage and waste treatment facilities.

Finally, skilled sewage system operators should also appreciate that the invented system allows for continuous processing of digestible wastes and FOG, in that the receiving/conditioning holding tank reservoirs the acid phase digestion of the FOG by the acidogens in actively digesting sludge, the low pH fatty acids precluding propagation of the methagens in the holding tank. The resultant slurry of digested FOG and sludge is a highly bioreactive, flowable, feedstock that can be metered over time into an actively digesting sludge stream and introduced at the input or head end of any anaerobic waste treatment cycle, not just an isolated a digester, along with other raw digestible wastes for continuous, as opposed to batch digestion, thus avoiding sharp (possibly explosive) methane production peaks. In short, preliminary results at the Millbrae Water Pollution Control Plant demonstrate an increase in steady-state methane production of more than 100%, and a significant reduction (50%) in digested solids volumes over and under that, respectively, which existed before integration of the FOG receiving system into the facility.

We claim:

1. A method comprising:
   introducing digesting sludge, at a temperature (T) high enough to soften FOG waste, into a holding tank;
   introducing FOG waste of a volume $V_H$ into the holding tank;
   mixing the digesting sludge and the FOG waste in the holding tank to form a conditioned feedstock; and
   transporting the conditioned feedstock to an anaerobic digester,
   wherein the digesting sludge is introduced from a lower portion of a secondary digester in an arrangement including at least first and second digesters.

2. The method of claim 1, wherein the temperature T is in the range of approximately 98° F. to 104° F.

3. The method of claim 1, wherein the mixing of the digesting sludge and the FOG waste decreases particle size in the FOG wastes in the conditioned feedstock.

4. The method of claim 3, wherein the mixing is achieved using at least one mixing chopper pump.

5. The method of claim 1, wherein introducing the digesting sludge includes introducing a first volume ($V_1$) of digesting sludge before introducing the FOG waste of a volume $V_H$ and introducing a second volume ($V_2$) of digesting sludge after introducing the FOG waste.

6. The method of claim 5, wherein the volumes $V_1$, $V_H$ and $V_2$ have a preselected relationship and $V_1+V_H+V_2$ is less than the volume of the holding tank.

7. The method of claim 5, further comprising allowing the introduced digesting sludge to react with the introduced FOG waste to form the conditioned feedstock.

8. The method of claim 5, wherein the digesting sludge is introduced from a slipstream loop along which the digesting sludge moves from the secondary digester to the primary digester.

9. The method of claim 8, wherein the digesting sludge is heated as it moves along the slipstream loop.

10. The method of claim 9 wherein the FOG waste is introduced into the holding tank through a delivery/input line and wherein the delivery/input line is preheated prior to introduction of the FOG waste into the holding tank.

11. The method of claim 10 wherein the FOG waste passes through a rock trap as it is introduced through the delivery/input line.

12. The method of claim 10 wherein the delivery/input line is preheated using digesting sludge from the slipstream loop.

13. The method of claim 12 wherein the digesting sludge used to preheat the delivery/input line is introduced into the holding tank as at least part of the first volume ($V_1$).

14. The method of claim 12 further comprising passing digesting sludge from the slipstream loop through the delivery/input line after the FOG waste is introduced into the holding tank.

15. The method of claim 14 wherein the digesting sludge introduced through the delivery/input line after the FOG waste is introduced into the holding tank is introduced into the holding tank as the second volume ($V_2$).

16. The method of claim 12, wherein the digesting sludge used to preheat the delivery/input line is introduced into the holding tank as at least part of the first volume ($V_1$).

17. The method of claim 9, further comprising maintaining a set minimum volume of liquid in the holding tank by filling the holding tank to the predetermined minimum volume when the holding tank level drops to a predetermined low level.

18. The method of claim 8, further comprising injecting conditioned feedstock from the holding tank into the slipstream loop at a point between the secondary and primary digesters to form a digesting sludge/conditioned feedstock mixture to transport the conditioned feedstock to the primary digester.

19. The method of claim 18, wherein the conditioned feedstock in the digesting sludge is carried along the slipstream loop at a rate sufficient to preclude FOG waste from separating from the digesting sludge.

20. The method of claim 1, wherein the conditioned feedstock is injected at a meterable rate into the digesting sludge slipstream loop.

21. A method comprising:
   introducing digesting sludge, at a temperature (T) high enough to soften FOG waste, into a holding tank;
   introducing FOG waste of a volume $V_H$ into the holding tank;
   mixing the digesting sludge and the FOG waste in the holding tank to form a conditioned feedstock, wherein the mixing of the digesting sludge and the FOG waste decreases particle size in the FOG wastes in the conditioned feedstock; and
   transporting the conditioned feedstock to an anaerobic digester.

22. The method of claim 21, wherein the digesting sludge is introduced from a lower portion of a secondary digester in an arrangement including at least first and second digesters.

23. The method of claim 21, wherein the temperature T is in the range of approximately 98° F. to 104° F.

24. The method of claim 21, wherein the mixing is achieved using at least one mixing chopper pump.

25. The method of claim 21, wherein introducing the digesting sludge includes introducing a first volume ($V_1$) of digesting sludge before introducing the FOG waste of a volume $V_H$ and introducing a second volume ($V_2$) of digesting sludge after introducing the FOG waste.

26. The method of claim 25, wherein the volumes $V_1$, $V_H$ and $V_2$ have a preselected relationship and $V_1+V_H+V_2$ is less than the volume of the holding tank.

27. The method of claim 25, further comprising allowing the introduced digesting sludge to react with the introduced FOG waste to form the conditioned feedstock.

28. The method of claim 25, wherein the digesting sludge is introduced from a slipstream loop along which the digesting sludge moves from the secondary digester to the primary digester.

29. The method of claim 28, wherein the digesting sludge is heated as it moves along the slipstream loop.

30. The method of claim 29, wherein the FOG waste is introduced into the holding tank through a delivery/input line and wherein the delivery/input line is preheated prior to introduction of the FOG waste into the holding tank.

31. The method of claim 30, wherein the FOG waste passes through a rock trap as it is introduced through the delivery/input line.

32. The method of claim 30, wherein the delivery/input line is preheated using digesting sludge from the slipstream loop.

33. The method of claim 32, further comprising passing digesting sludge from the slipstream loop through the delivery/input line after the FOG waste is introduced into the holding tank.

34. The method of claim 33, wherein the digesting sludge introduced through the delivery/input line after the FOG waste is introduced into the holding tank is introduced into the holding tank as the second volume ($V_2$).

35. The method of claim 29, further comprising maintaining a set minimum volume of liquid in the holding tank by filling the holding tank to the predetermined minimum volume when the holding tank level drops to a predetermined low level.

36. The method of claim 28, further comprising injecting conditioned feedstock from the holding tank into the slipstream loop at a point between the secondary and primary digesters to form a digesting sludge/conditioned feedstock mixture to transport the conditioned feedstock to the primary digester.

37. The method of claim 36, wherein the conditioned feedstock in the digesting sludge is carried along the slipstream loop at a rate sufficient to preclude FOG waste from separating from the digesting sludge.

38. The method of claim 21, wherein the conditioned feedstock is injected at a meterable rate into the digesting sludge slipstream loop.

39. A method comprising:
   introducing digesting sludge, at a temperature (T) high enough to soften FOG waste, into a holding tank;
   introducing FOG waste of a volume $V_H$ into the holding tank;
   mixing the digesting sludge and the FOG waste in the holding tank to form a conditioned feedstock; and
   transporting the conditioned feedstock to an anaerobic digester, wherein introducing the digesting sludge includes introducing a first volume ($V_1$) of digesting sludge before introducing the FOG waste of a volume $V_H$ and introducing a second volume ($V_2$) of digesting sludge after introducing the FOG waste.

40. The method of claim 39, wherein the digesting sludge is introduced from a lower portion of a secondary digester in an arrangement including at least first and second digesters.

41. The method of claim 39, wherein the temperature T is in the range of approximately 98° F. to 104° F.

42. The method of claim 39, wherein the mixing of the digesting sludge and the FOG waste decreases particle size in the FOG wastes in the conditioned feedstock.

43. The method of claim 39, wherein the mixing is achieved using at least one mixing chopper pump.

44. The method of claim 39, wherein the volumes $V_1$, $V_H$ and $V_2$ have a preselected relationship and $V_1+V_H+V_2$ is less than the volume of the holding tank.

45. The method of claim 39, further comprising allowing the introduced digesting sludge to react with the introduced FOG waste to form the conditioned feedstock.

46. The method of claim 39, wherein the digesting sludge is introduced from a slipstream loop along which the digesting sludge moves from the secondary digester to the primary digester.

47. The method of claim 46, wherein the digesting sludge is heated as it moves along the slipstream loop.

48. The method of claim 47, wherein the FOG waste is introduced into the holding tank through a delivery/input line and wherein the delivery/input line is preheated prior to introduction of the FOG waste into the holding tank.

49. The method of claim 48, wherein the FOG waste passes through a rock trap as it is introduced through the delivery/input line.

50. The method of claim 48, wherein the delivery/input line is preheated using digesting sludge from the slipstream loop.

51. The method of claim 50, wherein the digesting sludge used to preheat the delivery/input line is introduced into the holding tank as at least part of the first volume ($V_1$).

52. The method of claim 50, further comprising passing digesting sludge from the slipstream loop through the delivery/input line after the FOG waste is introduced into the holding tank.

53. The method of claim 52, wherein the digesting sludge introduced through the delivery/input line after the FOG waste is introduced into the holding tank is introduced into the holding tank as the second volume ($V_2$).

54. The method of claim 47, further comprising maintaining a set minimum volume of liquid in the holding tank by filling the holding tank to the predetermined minimum volume when the holding tank level drops to a predetermined low level.

55. The method of claim 46, further comprising injecting conditioned feedstock from the holding tank into the slipstream loop at a point between the secondary and primary digesters to form a digesting sludge/conditioned feedstock mixture to transport the conditioned feedstock to the primary digester.

56. The method of claim 55, wherein the conditioned feedstock in the digesting sludge is carried along the slipstream loop at a rate sufficient to preclude FOG waste from separating from the digesting sludge.

57. The method of claim 39, wherein the conditioned feedstock is injected at a meterable rate into the digesting sludge slipstream loop.

* * * * *